US008485993B2

(12) United States Patent
Orszulak et al.

(10) Patent No.: US 8,485,993 B2
(45) Date of Patent: *Jul. 16, 2013

(54) SWITCHED RESONANT ULTRASONIC POWER AMPLIFIER SYSTEM

(75) Inventors: James H. Orszulak, Nederland, CO (US); James W. McPherson, Boulder, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/350,877

(22) Filed: Jan. 16, 2012

(65) Prior Publication Data

US 2012/0116268 A1    May 10, 2012

Related U.S. Application Data

(63) Continuation of application No. 12/163,408, filed on Jun. 27, 2008, now Pat. No. 8,096,961, which is a continuation of application No. 10/974,332, filed on Oct. 27, 2004, now Pat. No. 7,396,336.

(60) Provisional application No. 60/538,202, filed on Jan. 22, 2004, provisional application No. 60/527,812, filed on Dec. 8, 2003, provisional application No. 60/515,826, filed on Oct. 30, 2003.

(51) Int. Cl.
   *A61F 7/00* (2006.01)
(52) U.S. Cl.
   USPC .................................. 601/2; 73/579; 607/96
(58) Field of Classification Search
   USPC ..... 73/662, 630; 601/2; 600/437; 606/27–52; 607/96
   See application file for complete search history.

(56) References Cited

U.S. PATENT DOCUMENTS

| | | | |
|---|---|---|---|
| 1,787,709 | A | 1/1931 | Wappler |
| 1,813,902 | A | 7/1931 | Bovie |
| 1,841,968 | A | 1/1932 | Lowry |
| 1,863,118 | A | 6/1932 | Liebel |
| 1,945,867 | A | 2/1934 | Rawls |
| 2,693,106 | A | 6/1951 | Henry |
| 2,827,056 | A | 3/1958 | Degelman |
| 2,849,611 | A | 8/1958 | Adams |
| 2,883,198 | A | 4/1959 | Narumi |

(Continued)

FOREIGN PATENT DOCUMENTS

| | | |
|---|---|---|
| DE | 179607 | 3/1905 |
| DE | 1099658 | 2/1961 |

(Continued)

OTHER PUBLICATIONS

US 6,878,148, 04/12/2005, Goble et al. (withdrawn).

(Continued)

*Primary Examiner* — J M Saint Surin

(57) ABSTRACT

A switched resonant power amplifier system for ultrasonic transducers is disclosed. The system includes an amplifier that receives and processes a driver output signal for generating a drive signal that is provided to an ultrasonic device for controlling output of the ultrasonic device. An output control circuit receives and processes a signal related to a feedback signal generated by the ultrasonic device and a divider reference signal, and generates a compensated clock signal that is adjusted for at least one of phase and frequency differences between the received feedback signal and the divider reference signal. A compensated drive circuit receives and processes the compensated clock signal for generating the divider reference signal, and for generating the driver output signal.

15 Claims, 2 Drawing Sheets

U.S. PATENT DOCUMENTS

| | | |
|---|---|---|
| 3,001,132 A | 9/1961 | Britt |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Beierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,938,072 A | 2/1976 | Baird et al. |
| 3,944,936 A | 3/1976 | Pryor |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,153,880 A | 5/1979 | Navratil |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gonser |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gonser |
| 4,247,815 A | 1/1981 | Larsen et al. |
| 4,271,837 A | 6/1981 | Schuler |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,430,625 A | 2/1984 | Yokoyama |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,580,575 A | 4/1986 | Birnbaum et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Paterson |
| 4,644,955 A | 2/1987 | Mioduski |
| 4,651,264 A | 3/1987 | Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |

| | | | | | |
|---|---|---|---|---|---|
| 4,754,757 A | 7/1988 | Feucht | 5,324,283 A | 6/1994 | Heckele |
| 4,767,999 A | 8/1988 | VerPlanck | 5,330,518 A | 7/1994 | Neilson et al. |
| 4,768,969 A | 9/1988 | Bauer et al. | 5,334,183 A | 8/1994 | Wuchinich |
| 4,785,829 A | 11/1988 | Convert et al. | 5,334,193 A | 8/1994 | Nardella |
| 4,788,634 A | 11/1988 | Schlecht et al. | 5,341,807 A | 8/1994 | Nardella |
| 4,805,621 A | 2/1989 | Heinze et al. | 5,342,356 A | 8/1994 | Ellman |
| 4,818,954 A | 4/1989 | Flachenecker et al. | 5,342,357 A | 8/1994 | Nardella |
| 4,827,927 A | 5/1989 | Newton | 5,342,409 A | 8/1994 | Mullett |
| 4,848,335 A | 7/1989 | Manes | 5,346,406 A | 9/1994 | Hoffman et al. |
| 4,860,745 A | 8/1989 | Farin et al. | 5,346,491 A | 9/1994 | Oertli |
| 4,862,889 A | 9/1989 | Feucht | 5,348,554 A | 9/1994 | Imran et al. |
| 4,887,199 A | 12/1989 | Whittle | 5,354,325 A | 10/1994 | Chive et al. |
| 4,890,610 A | 1/1990 | Kirwan et al. | 5,364,392 A | 11/1994 | Warner et al. |
| 4,903,696 A | 2/1990 | Stasz et al. | 5,369,567 A | 11/1994 | Furuta et al. |
| 4,907,589 A | 3/1990 | Cosman | 5,370,645 A | 12/1994 | Klicek et al. |
| 4,922,210 A | 5/1990 | Flachenecker et al. | 5,370,672 A | 12/1994 | Fowler et al. |
| 4,925,089 A | 5/1990 | Chaparro et al. | 5,370,675 A | 12/1994 | Edwards et al. |
| 4,931,047 A | 6/1990 | Broadwin et al. | 5,372,596 A | 12/1994 | Klicek et al. |
| 4,931,717 A | 6/1990 | Gray et al. | 5,383,874 A | 1/1995 | Jackson |
| 4,938,761 A | 7/1990 | Ensslin | 5,383,876 A | 1/1995 | Nardella |
| 4,942,313 A | 7/1990 | Kinzel | 5,383,917 A | 1/1995 | Desai et al. |
| 4,959,606 A | 9/1990 | Forge | 5,385,148 A | 1/1995 | Lesh et al. |
| 4,961,047 A | 10/1990 | Carder | 5,396,194 A | 3/1995 | Williamson et al. |
| 4,961,435 A | 10/1990 | Kitagawa et al. | 5,400,267 A | 3/1995 | Denen et al. |
| 4,966,597 A | 10/1990 | Cosman | 5,403,311 A | 4/1995 | Abele et al. |
| 4,969,885 A | 11/1990 | Farin | 5,403,312 A | 4/1995 | Yates et al. |
| 4,992,719 A | 2/1991 | Harvey | 5,409,000 A | 4/1995 | Imran |
| 4,993,430 A | 2/1991 | Shimoyama et al. | 5,409,485 A | 4/1995 | Suda |
| 4,995,877 A | 2/1991 | Ams et al. | 5,413,573 A | 5/1995 | Koivukangas |
| 5,015,227 A | 5/1991 | Broadwin et al. | 5,414,238 A | 5/1995 | Steigerwald et al. |
| 5,024,668 A | 6/1991 | Peters et al. | 5,417,719 A | 5/1995 | Hull et al. |
| 5,044,977 A | 9/1991 | Vindigni | 5,422,567 A | 6/1995 | Matsunaga |
| 5,057,105 A | 10/1991 | Malone et al. | 5,422,926 A | 6/1995 | Smith et al. |
| 5,067,953 A | 11/1991 | Feucht | 5,423,808 A | 6/1995 | Edwards et al. |
| 5,075,839 A | 12/1991 | Fisher et al. | 5,423,809 A | 6/1995 | Klicek |
| 5,078,153 A | 1/1992 | Nordlander et al. | 5,423,810 A | 6/1995 | Goble et al. |
| 5,087,257 A | 2/1992 | Farin | 5,423,811 A | 6/1995 | Imran et al. |
| 5,099,840 A | 3/1992 | Goble et al. | 5,425,704 A | 6/1995 | Sakurai et al. |
| 5,103,804 A | 4/1992 | Abele et al. | 5,429,596 A | 7/1995 | Arias et al. |
| 5,108,389 A | 4/1992 | Cosmescu | 5,430,434 A | 7/1995 | Lederer et al. |
| 5,108,391 A | 4/1992 | Flachenecker | 5,432,459 A | 7/1995 | Thompson |
| 5,113,116 A | 5/1992 | Wilson | 5,433,739 A | 7/1995 | Sluijter et al. |
| 5,119,284 A | 6/1992 | Fisher et al. | 5,436,566 A | 7/1995 | Thompson |
| 5,122,137 A | 6/1992 | Lennox | 5,438,302 A | 8/1995 | Goble |
| 5,133,711 A | 7/1992 | Hagen | 5,443,462 A | 8/1995 | Hannant |
| 5,151,102 A | 9/1992 | Kamiyama et al. | 5,443,463 A | 8/1995 | Stern et al. |
| 5,152,762 A | 10/1992 | McElhenney | 5,445,635 A | 8/1995 | Denen |
| 5,157,603 A | 10/1992 | Scheller et al. | 5,445,638 A | 8/1995 | Rydell et al. |
| 5,160,334 A | 11/1992 | Billings et al. | 5,448,466 A | 9/1995 | Erckert |
| 5,161,893 A | 11/1992 | Shigezawa et al. | 5,451,224 A | 9/1995 | Goble et al. |
| 5,167,658 A | 12/1992 | Ensslin | 5,452,725 A | 9/1995 | Martenson |
| 5,167,659 A | 12/1992 | Ohtomo et al. | 5,454,809 A | 10/1995 | Janssen |
| 5,190,517 A | 3/1993 | Zieve et al. | 5,458,597 A | 10/1995 | Edwards et al. |
| 5,196,008 A | 3/1993 | Kuenecke | 5,462,521 A | 10/1995 | Brucker et al. |
| 5,196,009 A | 3/1993 | Kirwan, Jr. | 5,472,441 A | 12/1995 | Edwards et al. |
| 5,201,900 A | 4/1993 | Nardella | 5,472,443 A | 12/1995 | Cordis et al. |
| 5,207,691 A | 5/1993 | Nardella | 5,474,464 A | 12/1995 | Drewnicki |
| 5,216,338 A | 6/1993 | Wilson | 5,480,399 A | 1/1996 | Hebborn |
| 5,230,623 A | 7/1993 | Guthrie et al. | 5,483,952 A | 1/1996 | Aranyi |
| 5,233,515 A | 8/1993 | Cosman | 5,496,312 A | 3/1996 | Klicek |
| 5,234,427 A | 8/1993 | Ohtomo et al. | 5,496,313 A | 3/1996 | Gentelia et al. |
| 5,244,462 A | 9/1993 | Delahuerga et al. | 5,496,314 A | 3/1996 | Eggers |
| 5,249,121 A | 9/1993 | Baum et al. | 5,498,261 A | 3/1996 | Strul |
| 5,249,585 A | 10/1993 | Turner et al. | 5,500,012 A | 3/1996 | Brucker et al. |
| 5,254,117 A | 10/1993 | Rigby et al. | 5,500,616 A | 3/1996 | Ochi |
| RE34,432 E | 11/1993 | Bertrand | 5,511,993 A | 4/1996 | Yamada et al. |
| 5,267,994 A | 12/1993 | Gentelia et al. | 5,514,129 A | 5/1996 | Smith |
| 5,267,997 A | 12/1993 | Farin | 5,520,684 A | 5/1996 | Imran |
| 5,269,780 A | 12/1993 | Roos | 5,531,774 A | 7/1996 | Schulman et al. |
| 5,271,413 A | 12/1993 | Dalamagas et al. | 5,534,018 A | 7/1996 | Wahlstrand et al. |
| 5,281,213 A | 1/1994 | Milder et al. | 5,536,267 A | 7/1996 | Edwards et al. |
| 5,282,840 A | 2/1994 | Hudrlik | 5,540,677 A | 7/1996 | Sinofsky |
| 5,290,283 A | 3/1994 | Suda | 5,540,681 A | 7/1996 | Strul et al. |
| 5,295,857 A | 3/1994 | Toly | 5,540,682 A | 7/1996 | Gardner et al. |
| 5,300,068 A | 4/1994 | Rosar et al. | 5,540,683 A | 7/1996 | Ichikawa |
| 5,300,070 A | 4/1994 | Gentelia | 5,540,684 A | 7/1996 | Hassler, Jr. |
| 5,304,917 A | 4/1994 | Somerville | 5,541,376 A | 7/1996 | Ladtkow et al. |
| 5,318,563 A | 6/1994 | Malis et al. | 5,542,916 A | 8/1996 | Hirsch et al. |
| 5,323,778 A | 6/1994 | Kandarpa et al. | 5,545,161 A | 8/1996 | Imran |

| | | | | | | |
|---|---|---|---|---|---|---|
| 5,554,172 A | 9/1996 | Horner et al. | | 5,830,212 A | 11/1998 | Cartmell |
| 5,556,396 A | 9/1996 | Cohen et al. | | 5,831,166 A | 11/1998 | Kozuka et al. |
| 5,558,671 A | 9/1996 | Yates | | 5,836,909 A | 11/1998 | Cosmescu |
| 5,559,688 A | 9/1996 | Pringle | | 5,836,943 A | 11/1998 | Miller, III |
| 5,562,720 A | 10/1996 | Stern et al. | | 5,836,990 A | 11/1998 | Li |
| 5,569,242 A | 10/1996 | Lax et al. | | 5,843,019 A | 12/1998 | Eggers et al. |
| 5,571,147 A | 11/1996 | Sluijter et al. | | 5,843,075 A | 12/1998 | Taylor |
| 5,573,533 A | 11/1996 | Strul | | 5,846,236 A | 12/1998 | Lindenmeier et al. |
| 5,584,830 A | 12/1996 | Ladd et al. | | 5,849,010 A | 12/1998 | Wurzer et al. |
| 5,588,432 A | 12/1996 | Crowley | | 5,853,409 A | 12/1998 | Swanson et al. |
| 5,596,466 A | 1/1997 | Ochi | | 5,860,832 A | 1/1999 | Wayt et al. |
| 5,596,995 A | 1/1997 | Sherman et al. | | 5,865,788 A | 2/1999 | Edwards et al. |
| 5,599,344 A | 2/1997 | Paterson | | 5,868,737 A | 2/1999 | Taylor et al. |
| 5,599,345 A | 2/1997 | Edwards et al. | | 5,868,739 A | 2/1999 | Lindenmeier et al. |
| 5,599,348 A | 2/1997 | Gentelia et al. | | 5,868,740 A | 2/1999 | LeVeen et al. |
| 5,605,150 A | 2/1997 | Radons et al. | | 5,871,481 A | 2/1999 | Kannenberg et al. |
| 5,609,560 A | 3/1997 | Ichikawa et al. | | 5,891,142 A | 4/1999 | Eggers et al. |
| 5,613,966 A | 3/1997 | Makower et al. | | 5,893,848 A | 4/1999 | Negus et al. |
| 5,620,481 A | 4/1997 | Desai et al. | | 5,897,552 A | 4/1999 | Edwards et al. |
| 5,626,575 A | 5/1997 | Crenner | | 5,906,614 A | 5/1999 | Stern et al. |
| 5,628,745 A | 5/1997 | Bek | | 5,908,444 A | 6/1999 | Azure |
| 5,628,771 A | 5/1997 | Mizukawa et al. | | 5,913,882 A | 6/1999 | King |
| 5,633,578 A | 5/1997 | Eggers et al. | | 5,921,982 A | 7/1999 | Lesh et al. |
| 5,640,113 A | 6/1997 | Hu | | 5,925,070 A | 7/1999 | King et al. |
| 5,643,330 A | 7/1997 | Holsheimer et al. | | 5,931,836 A | 8/1999 | Hatta et al. |
| 5,647,869 A | 7/1997 | Goble et al. | | 5,935,124 A | 8/1999 | Klumb et al. |
| 5,647,871 A | 7/1997 | Levine et al. | | 5,938,690 A | 8/1999 | Law et al. |
| 5,651,780 A | 7/1997 | Jackson et al. | | 5,944,553 A | 8/1999 | Yasui et al. |
| 5,658,322 A | 8/1997 | Fleming | | 5,948,007 A | 9/1999 | Starkebaum et al. |
| 5,660,567 A | 8/1997 | Nierlich et al. | | 5,951,545 A | 9/1999 | Schilling |
| 5,664,953 A | 9/1997 | Reylek | | 5,951,546 A | 9/1999 | Lorentzen |
| 5,674,217 A | 10/1997 | Wahlstrom et al. | | 5,954,686 A | 9/1999 | Garito et al. |
| 5,675,609 A | 10/1997 | Johnson | | 5,954,717 A | 9/1999 | Behl et al. |
| 5,678,568 A | 10/1997 | Uchikubo et al. | | 5,954,719 A | 9/1999 | Chen et al. |
| 5,681,307 A | 10/1997 | McMahan | | 5,957,961 A | 9/1999 | Maguire et al. |
| 5,685,840 A | 11/1997 | Schechter et al. | | 5,957,969 A | 9/1999 | Warner et al. |
| 5,688,267 A | 11/1997 | Panescu et al. | | 5,959,253 A | 9/1999 | Shinchi |
| 5,693,042 A | 12/1997 | Boiarski et al. | | 5,961,344 A | 10/1999 | Rosales et al. |
| 5,693,078 A | 12/1997 | Desai et al. | | 5,961,871 A | 10/1999 | Bible et al. |
| 5,694,304 A | 12/1997 | Telefus et al. | | 5,964,746 A | 10/1999 | McCary |
| 5,695,494 A | 12/1997 | Becker | | 5,971,980 A | 10/1999 | Sherman |
| 5,696,441 A | 12/1997 | Mak et al. | | 5,971,981 A | 10/1999 | Hill et al. |
| 5,697,925 A | 12/1997 | Taylor | | 5,976,128 A | 11/1999 | Schilling et al. |
| 5,697,927 A | 12/1997 | Imran et al. | | 5,983,141 A | 11/1999 | Sluijter et al. |
| 5,702,386 A | 12/1997 | Stern et al. | | 5,999,848 A | 12/1999 | Gord et al. |
| 5,702,429 A | 12/1997 | King | | 6,007,532 A | 12/1999 | Netherly |
| 5,707,369 A | 1/1998 | Vaitekunas et al. | | 6,010,499 A | 1/2000 | Cobb |
| 5,712,772 A | 1/1998 | Telefus et al. | | 6,013,074 A | 1/2000 | Taylor |
| 5,713,896 A | 2/1998 | Nardella | | 6,014,581 A | 1/2000 | Whayne et al. |
| 5,718,246 A | 2/1998 | Vona | | 6,017,338 A | 1/2000 | Brucker et al. |
| 5,720,742 A | 2/1998 | Zacharias | | 6,017,354 A | 1/2000 | Culp et al. |
| 5,720,744 A | 2/1998 | Eggleston et al. | | 6,022,346 A | 2/2000 | Panescu et al. |
| 5,722,975 A | 3/1998 | Edwards et al. | | 6,022,347 A | 2/2000 | Lindenmeier et al. |
| 5,729,448 A | 3/1998 | Haynie et al. | | 6,033,399 A | 3/2000 | Gines |
| 5,733,281 A | 3/1998 | Nardella | | 6,039,731 A | 3/2000 | Taylor et al. |
| 5,735,846 A | 4/1998 | Panescu et al. | | 6,039,732 A | 3/2000 | Ichikawa et al. |
| 5,738,683 A | 4/1998 | Osypka | | 6,041,260 A | 3/2000 | Stern et al. |
| 5,743,900 A | 4/1998 | Hara | | 6,044,283 A | 3/2000 | Fein et al. |
| 5,743,903 A | 4/1998 | Stern et al. | | 6,053,910 A | 4/2000 | Fleenor |
| 5,749,869 A | 5/1998 | Lindenmeier et al. | | 6,053,912 A | 4/2000 | Panescu et al. |
| 5,749,871 A | 5/1998 | Hood et al. | | 6,055,458 A | 4/2000 | Cochran et al. |
| 5,755,715 A | 5/1998 | Stern | | 6,056,745 A | 5/2000 | Panescu et al. |
| 5,762,609 A | 6/1998 | Benaron et al. | | 6,056,746 A | 5/2000 | Goble et al. |
| 5,766,153 A | 6/1998 | Eggers et al. | | 6,059,780 A | 5/2000 | Gough et al. |
| 5,766,165 A | 6/1998 | Gentelia et al. | | 6,059,781 A | 5/2000 | Yamanashi et al. |
| 5,769,847 A | 6/1998 | Panescu | | 6,063,075 A | 5/2000 | Mihori |
| 5,772,659 A | 6/1998 | Becker et al. | | 6,063,078 A | 5/2000 | Wittkampf |
| 5,777,519 A | 7/1998 | Simopoulos | | 6,066,137 A | 5/2000 | Greep |
| 5,788,688 A | 8/1998 | Bauer et al. | | 6,068,627 A | 5/2000 | Orszulak et al. |
| 5,792,138 A | 8/1998 | Shipp | | 6,074,089 A | 6/2000 | Hollander et al. |
| 5,797,902 A | 8/1998 | Netherly | | 6,074,386 A | 6/2000 | Goble et al. |
| 5,797,941 A | 8/1998 | Schulze et al. | | 6,074,388 A | 6/2000 | Tockweiler et al. |
| 5,807,253 A | 9/1998 | Dumoulin et al. | | 6,080,149 A | 6/2000 | Huang et al. |
| 5,810,804 A | 9/1998 | Gough et al. | | 6,088,614 A | 7/2000 | Swanson |
| 5,814,092 A | 9/1998 | King | | 6,089,864 A | 7/2000 | Buckner et al. |
| 5,817,091 A | 10/1998 | Nardella et al. | | 6,090,123 A | 7/2000 | Culp et al. |
| 5,817,093 A | 10/1998 | Williamson, IV et al. | | 6,093,186 A | 7/2000 | Goble |
| 5,820,568 A | 10/1998 | Willis | | 6,102,497 A | 8/2000 | Ehr et al. |
| 5,827,271 A | 10/1998 | Bussey et al. | | 6,102,907 A | 8/2000 | Smethers et al. |

| Patent | Type | Date | Inventor |
|---|---|---|---|
| 6,104,248 | A | 8/2000 | Carver |
| 6,106,524 | A | 8/2000 | Eggers et al. |
| 6,113,591 | A | 9/2000 | Whayne et al. |
| 6,113,592 | A | 9/2000 | Taylor |
| 6,113,593 | A | 9/2000 | Tu et al. |
| 6,113,596 | A | 9/2000 | Hooven |
| 6,123,701 | A | 9/2000 | Nezhat |
| 6,123,702 | A | 9/2000 | Swanson et al. |
| 6,132,429 | A | 10/2000 | Baker |
| 6,139,349 | A | 10/2000 | Wright |
| 6,142,992 | A | 11/2000 | Cheng et al. |
| 6,155,975 | A | 12/2000 | Urich et al. |
| 6,162,184 | A | 12/2000 | Swanson et al. |
| 6,162,217 | A | 12/2000 | Kannenberg et al. |
| 6,165,169 | A | 12/2000 | Panescu et al. |
| 6,165,173 | A | 12/2000 | Kamdar et al. |
| 6,171,304 | B1 | 1/2001 | Netherly et al. |
| 6,183,468 | B1 | 2/2001 | Swanson et al. |
| 6,186,147 | B1 | 2/2001 | Cobb |
| 6,188,211 | B1 | 2/2001 | Rincon-Mora et al. |
| 6,193,713 | B1 | 2/2001 | Geistert et al. |
| 6,197,023 | B1 | 3/2001 | Muntermann |
| 6,203,541 | B1 | 3/2001 | Keppel |
| 6,210,403 | B1 | 4/2001 | Klicek |
| 6,216,704 | B1 | 4/2001 | Ingle et al. |
| 6,222,356 | B1 | 4/2001 | Taghizadeh-Kaschani |
| 6,228,078 | B1 | 5/2001 | Eggers et al. |
| 6,228,080 | B1 | 5/2001 | Gines |
| 6,228,081 | B1 | 5/2001 | Goble |
| 6,231,569 | B1 | 5/2001 | Bek |
| 6,232,556 | B1 | 5/2001 | Daugherty et al. |
| 6,235,020 | B1 | 5/2001 | Cheng et al. |
| 6,235,022 | B1 | 5/2001 | Hallock et al. |
| 6,237,604 | B1 | 5/2001 | Burnside et al. |
| 6,238,387 | B1 | 5/2001 | Miller, III |
| 6,238,388 | B1 | 5/2001 | Ellman |
| 6,241,723 | B1 | 6/2001 | Heim et al. |
| 6,241,725 | B1 | 6/2001 | Cosman |
| 6,243,654 | B1 | 6/2001 | Johnson et al. |
| 6,245,061 | B1 | 6/2001 | Panescu et al. |
| 6,245,063 | B1 | 6/2001 | Uphoff |
| 6,245,065 | B1 | 6/2001 | Panescu |
| 6,246,912 | B1 | 6/2001 | Sluijter et al. |
| 6,251,106 | B1 | 6/2001 | Becker et al. |
| 6,254,422 | B1 | 7/2001 | Feye-Hohmann |
| 6,258,085 | B1 | 7/2001 | Eggleston |
| 6,259,937 | B1 | 7/2001 | Schulman et al. |
| 6,261,285 | B1 | 7/2001 | Novak |
| 6,261,286 | B1 | 7/2001 | Goble et al. |
| 6,267,760 | B1 | 7/2001 | Swanson |
| 6,270,497 | B1 | 8/2001 | Sekino et al. |
| 6,273,886 | B1 | 8/2001 | Edwards |
| 6,275,786 | B1 | 8/2001 | Daners |
| 6,287,304 | B1 | 9/2001 | Eggers et al. |
| 6,293,941 | B1 | 9/2001 | Strul |
| 6,293,942 | B1 | 9/2001 | Goble et al. |
| 6,293,943 | B1 | 9/2001 | Panescu et al. |
| 6,296,636 | B1 | 10/2001 | Cheng et al. |
| 6,304,138 | B1 | 10/2001 | Johnson |
| 6,306,131 | B1 | 10/2001 | Hareyama et al. |
| 6,306,134 | B1 | 10/2001 | Goble et al. |
| 6,309,386 | B1 | 10/2001 | Bek |
| 6,322,558 | B1 | 11/2001 | Taylor et al. |
| 6,325,799 | B1 | 12/2001 | Goble |
| 6,329,778 | B1 | 12/2001 | Culp et al. |
| 6,337,998 | B1 | 1/2002 | Behl et al. |
| 6,338,657 | B1 | 1/2002 | Harper et al. |
| 6,341,981 | B1 | 1/2002 | Gorman |
| 6,350,262 | B1 | 2/2002 | Ashley |
| 6,358,245 | B1 | 3/2002 | Edwards |
| 6,364,877 | B1 | 4/2002 | Goble et al. |
| 6,370,408 | B1 | 4/2002 | Merchant et al. |
| 6,371,963 | B1 | 4/2002 | Nishtala et al. |
| 6,383,183 | B1 | 5/2002 | Sekino et al. |
| 6,387,092 | B1 | 5/2002 | Burnside et al. |
| 6,391,024 | B1 | 5/2002 | Sun et al. |
| 6,398,779 | B1 | 6/2002 | Buysse et al. |
| 6,398,781 | B1 | 6/2002 | Goble et al. |
| 6,402,741 | B1 | 6/2002 | Keppel et al. |
| 6,402,742 | B1 | 6/2002 | Blewett et al. |
| 6,402,743 | B1 | 6/2002 | Orszulak et al. |
| 6,402,748 | B1 | 6/2002 | Schoenman et al. |
| 6,409,722 | B1 | 6/2002 | Hoey et al. |
| 6,413,256 | B1 | 7/2002 | Truckai et al. |
| 6,416,509 | B1 | 7/2002 | Goble et al. |
| 6,422,896 | B2 | 7/2002 | Aoki et al. |
| 6,423,057 | B1 | 7/2002 | He et al. |
| 6,424,186 | B1 | 7/2002 | Quimby et al. |
| 6,426,886 | B1 | 7/2002 | Goder |
| 6,428,537 | B1 | 8/2002 | Swanson et al. |
| 6,436,096 | B1 | 8/2002 | Hareyama |
| 6,440,157 | B1 | 8/2002 | Shigezawa et al. |
| 6,451,015 | B1 | 9/2002 | Rittman, III et al. |
| 6,454,594 | B2 | 9/2002 | Sawayanagi |
| 6,458,121 | B1 | 10/2002 | Rosenstock |
| 6,458,122 | B1 | 10/2002 | Pozzato |
| 6,464,689 | B1 | 10/2002 | Qin |
| 6,464,696 | B1 | 10/2002 | Oyama |
| 6,468,270 | B1 | 10/2002 | Hovda et al. |
| 6,468,273 | B1 | 10/2002 | Leveen et al. |
| 6,469,481 | B1 | 10/2002 | Tateishi |
| 6,482,201 | B1 | 11/2002 | Olsen et al. |
| 6,488,678 | B2 | 12/2002 | Sherman |
| 6,494,880 | B1 | 12/2002 | Swanson et al. |
| 6,497,659 | B1 | 12/2002 | Rafert |
| 6,498,466 | B1 | 12/2002 | Edwards |
| 6,506,189 | B1 | 1/2003 | Rittman, III et al. |
| 6,508,815 | B1 | 1/2003 | Strul |
| 6,511,476 | B1 | 1/2003 | Hareyama |
| 6,511,478 | B1 | 1/2003 | Burnside |
| 6,517,538 | B1 | 2/2003 | Jacob et al. |
| 6,522,931 | B2 | 2/2003 | Manker et al. |
| 6,524,308 | B1 | 2/2003 | Muller et al. |
| 6,537,272 | B2 | 3/2003 | Christopherson et al. |
| 6,544,258 | B2 | 4/2003 | Fleenor et al. |
| 6,544,260 | B1 | 4/2003 | Markel et al. |
| 6,546,270 | B1 | 4/2003 | Goldin et al. |
| 6,547,786 | B1 | 4/2003 | Goble |
| 6,557,559 | B1 | 5/2003 | Eggers et al. |
| 6,558,376 | B2 | 5/2003 | Bishop |
| 6,558,377 | B2 | 5/2003 | Lee et al. |
| 6,560,470 | B1 | 5/2003 | Pologe |
| 6,562,037 | B2 | 5/2003 | Paton |
| 6,565,559 | B2 | 5/2003 | Eggleston |
| 6,565,562 | B1 | 5/2003 | Shah et al. |
| 6,575,969 | B1 | 6/2003 | Rittman, III et al. |
| 6,578,579 | B2 | 6/2003 | Burnside et al. |
| 6,579,288 | B1 | 6/2003 | Swanson et al. |
| 6,582,427 | B1 | 6/2003 | Goble et al. |
| 6,602,243 | B2 | 8/2003 | Noda |
| 6,602,252 | B2 | 8/2003 | Mollenauer |
| 6,611,793 | B1 | 8/2003 | Burnside et al. |
| 6,620,157 | B1 | 9/2003 | Dabney et al. |
| 6,620,189 | B1 | 9/2003 | Machold et al. |
| 6,623,423 | B2 | 9/2003 | Sakurai |
| 6,626,901 | B1 | 9/2003 | Treat et al. |
| 6,629,973 | B1 | 10/2003 | Wardell et al. |
| 6,629,974 | B2 | 10/2003 | Penny et al. |
| 6,632,193 | B1 | 10/2003 | Davison et al. |
| 6,635,056 | B2 | 10/2003 | Kadhiresan et al. |
| 6,635,057 | B2 | 10/2003 | Harano |
| 6,645,198 | B1 | 11/2003 | Bommannan et al. |
| 6,648,883 | B2 | 11/2003 | Francischelli |
| 6,651,669 | B1 | 11/2003 | Burnside |
| 6,652,513 | B2 | 11/2003 | Panescu et al. |
| 6,652,514 | B2 | 11/2003 | Ellman |
| 6,653,569 | B1 | 11/2003 | Sung |
| 6,656,177 | B2 | 12/2003 | Truckai et al. |
| 6,663,623 | B1 | 12/2003 | Oyama et al. |
| 6,663,624 | B2 | 12/2003 | Edwards et al. |
| 6,663,627 | B2 | 12/2003 | Francischelli et al. |
| 6,666,860 | B1 | 12/2003 | Takahashi |
| 6,672,151 | B1 | 1/2004 | Schultz et al. |
| 6,679,875 | B2 | 1/2004 | Honda |
| 6,682,527 | B2 | 1/2004 | Strul |
| 6,685,700 | B2 | 2/2004 | Behl |
| 6,685,701 | B2 | 2/2004 | Orszulak et al. |
| 6,685,703 | B2 | 2/2004 | Pearson et al. |

| Patent No. | Date | Inventor |
|---|---|---|
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,775,575 B2 | 8/2004 | Bommannan et al. |
| 6,778,044 B2 | 8/2004 | Fehrenbach et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,788,977 B2 | 9/2004 | Fenn et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,819,027 B2 | 11/2004 | Saraf |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,887,240 B1 | 5/2005 | Lands et al. |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,979,329 B2 | 12/2005 | Burnside et al. |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,058,372 B1 | 6/2006 | Pardoen et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,087,054 B2 | 8/2006 | Truckai et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,184,820 B2 | 2/2007 | Jersey-Willuhn et al. |
| 7,190,933 B2 | 3/2007 | DeRuijter et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,204,835 B2 | 4/2007 | Latterell et al. |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,241,296 B2 | 7/2007 | Buysse et al. |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,269,034 B2 | 9/2007 | Schlecht |
| 7,276,068 B2 | 10/2007 | Johnson et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,311,703 B2 | 12/2007 | Turovskiy et al. |
| 7,316,682 B2 | 1/2008 | Konesky |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |

| Patent Number | Date | Inventor |
|---|---|---|
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,511,472 B1 | 3/2009 | Xia et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,568,619 B2 | 8/2009 | Todd et al. |
| 7,582,084 B2 | 9/2009 | Swanson et al. |
| 7,621,041 B2 | 11/2009 | Banerji et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,666,182 B2 | 2/2010 | Klett et al. |
| 7,675,429 B2 | 3/2010 | Cernasov |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,744,593 B2 | 6/2010 | Mihori |
| 7,749,217 B2 | 7/2010 | Podhajsky |
| 7,766,693 B2 | 8/2010 | Sartor et al. |
| 7,766,905 B2 | 8/2010 | Paterson et al. |
| 7,780,662 B2 | 8/2010 | Bahney |
| 7,780,764 B2 | 8/2010 | Baksh |
| 7,794,457 B2 | 9/2010 | McPherson et al. |
| 7,799,020 B2 | 9/2010 | Shores et al. |
| 7,799,026 B2 | 9/2010 | Schechter et al. |
| 7,824,400 B2 | 11/2010 | Keppel |
| 7,834,484 B2 | 11/2010 | Sartor |
| 7,863,841 B2 | 1/2011 | Menegoli et al. |
| 7,864,129 B2 | 1/2011 | Konishi |
| 7,879,033 B2 | 2/2011 | Sartor et al. |
| 7,901,400 B2 | 3/2011 | Wham et al. |
| 7,927,328 B2 | 4/2011 | Orszulak et al. |
| 7,947,039 B2 | 5/2011 | Sartor |
| 7,956,620 B2 | 6/2011 | Gilbert |
| 7,959,626 B2 | 6/2011 | Hong et al. |
| 7,972,328 B2 | 7/2011 | Wham et al. |
| 7,972,332 B2 | 7/2011 | Arts et al. |
| 7,976,544 B2 | 7/2011 | McClurken et al. |
| 8,004,121 B2 | 8/2011 | Sartor |
| 8,012,150 B2 | 9/2011 | Wham et al. |
| 8,025,660 B2 | 9/2011 | Plaven et al. |
| 8,034,049 B2 | 10/2011 | Odom et al. |
| 8,038,676 B2 | 10/2011 | Fischer |
| 8,080,008 B2 | 12/2011 | Wham et al. |
| 8,096,961 B2 | 1/2012 | Orszulak et al. |
| 8,104,596 B2 | 1/2012 | Kim et al. |
| 8,105,323 B2 | 1/2012 | Buysse et al. |
| 8,113,057 B2 | 2/2012 | Orszulak et al. |
| 8,133,218 B2 | 3/2012 | Daw et al. |
| 8,133,222 B2 | 3/2012 | Ormsby |
| 8,147,485 B2 | 4/2012 | Wham et al. |
| 8,152,800 B2 | 4/2012 | Behnke |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,167,875 B2 | 5/2012 | Podhajsky et al. |
| 2002/0029036 A1 | 3/2002 | Goble et al. |
| 2003/0153908 A1 | 8/2003 | Goble et al. |
| 2003/0181898 A1 | 9/2003 | Bowers |
| 2003/0229344 A1 | 12/2003 | Dycus et al. |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0133189 A1 | 7/2004 | Sakurai |
| 2004/0172016 A1 | 9/2004 | Bek et al. |
| 2004/0193021 A1 | 9/2004 | Zdeblick et al. |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0109935 A1 | 5/2005 | Manlove et al. |
| 2005/0131390 A1 | 6/2005 | Heinrich et al. |
| 2006/0015095 A1 | 1/2006 | Desinger et al. |
| 2006/0079774 A1 | 4/2006 | Anderson |
| 2006/0111711 A1 | 5/2006 | Goble |
| 2006/0155270 A1 | 7/2006 | Hancock et al. |
| 2006/0161148 A1 | 7/2006 | Behnke |
| 2006/0191926 A1 | 8/2006 | Ray et al. |
| 2006/0224053 A1 | 10/2006 | Black et al. |
| 2006/0224152 A1 | 10/2006 | Behnke et al. |
| 2006/0291178 A1 | 12/2006 | Shih |
| 2007/0088413 A1 | 4/2007 | Weber et al. |
| 2007/0093801 A1 | 4/2007 | Behnke |
| 2007/0173802 A1 | 7/2007 | Keppel |
| 2007/0173803 A1 | 7/2007 | Wham et al. |
| 2007/0173805 A1 | 7/2007 | Weinberg et al. |
| 2007/0173811 A1 | 7/2007 | Couture et al. |
| 2007/0173813 A1 | 7/2007 | Odom |
| 2007/0203481 A1 | 8/2007 | Gregg et al. |
| 2007/0265612 A1 | 11/2007 | Behnke et al. |
| 2007/0282320 A1 | 12/2007 | Buysse et al. |
| 2008/0004619 A1 | 1/2008 | Malis et al. |
| 2008/0015563 A1 | 1/2008 | Hoey et al. |
| 2008/0015570 A1 | 1/2008 | Ormsby et al. |
| 2008/0071257 A1 | 3/2008 | Kotmel et al. |
| 2008/0071260 A1 | 3/2008 | Shores |
| 2008/0119843 A1 | 5/2008 | Morris |
| 2008/0132893 A1 | 6/2008 | D'Amelio et al. |
| 2008/0177199 A1 | 7/2008 | Podhajsky |
| 2008/0203997 A1 | 8/2008 | Foran et al. |
| 2008/0234574 A1 | 9/2008 | Hancock et al. |
| 2008/0262489 A1 | 10/2008 | Steinke |
| 2008/0281311 A1 | 11/2008 | Dunning et al. |
| 2008/0281315 A1 | 11/2008 | Gines |
| 2008/0281316 A1 | 11/2008 | Carlton et al. |
| 2008/0287943 A1 | 11/2008 | Weber et al. |
| 2009/0018536 A1 | 1/2009 | Behnke |
| 2009/0069801 A1 | 3/2009 | Jensen et al. |
| 2009/0082765 A1 | 3/2009 | Collins et al. |
| 2009/0146635 A1 | 6/2009 | Qiu et al. |
| 2009/0157071 A1 | 6/2009 | Wham et al. |
| 2009/0157072 A1 | 6/2009 | Wham et al. |
| 2009/0157073 A1 | 6/2009 | Orszulak |
| 2009/0234350 A1 | 9/2009 | Behnke et al. |
| 2009/0237169 A1 | 9/2009 | Orszulak |
| 2009/0240244 A1 | 9/2009 | Malis et al. |
| 2009/0248003 A1 | 10/2009 | Orszulak |
| 2009/0248006 A1 | 10/2009 | Paulus et al. |
| 2009/0248007 A1 | 10/2009 | Falkenstein et al. |
| 2009/0254077 A1 | 10/2009 | Craig |
| 2009/0259224 A1 | 10/2009 | Wham et al. |
| 2009/0292283 A1 | 11/2009 | Odom |
| 2009/0306648 A1 | 12/2009 | Podhajsky et al. |
| 2010/0030210 A1 | 2/2010 | Paulus |
| 2010/0042093 A9 | 2/2010 | Wham et al. |
| 2010/0057076 A1 | 3/2010 | Behnke et al. |
| 2010/0063494 A1 | 3/2010 | Orszulak |
| 2010/0063497 A1 | 3/2010 | Orszulak |
| 2010/0076424 A1 | 3/2010 | Carr |
| 2010/0079215 A1 | 4/2010 | Brannan et al. |
| 2010/0082022 A1 | 4/2010 | Haley et al. |
| 2010/0082023 A1 | 4/2010 | Brannan et al. |
| 2010/0082024 A1 | 4/2010 | Brannan et al. |
| 2010/0082025 A1 | 4/2010 | Brannan et al. |

| Publication No. | Date | Inventor |
|---|---|---|
| 2010/0082083 A1 | 4/2010 | Brannan et al. |
| 2010/0082084 A1 | 4/2010 | Brannan et al. |
| 2010/0094271 A1 | 4/2010 | Ward et al. |
| 2010/0094275 A1 | 4/2010 | Wham |
| 2010/0094288 A1 | 4/2010 | Kerr |
| 2010/0114090 A1 | 5/2010 | Hosier |
| 2010/0168730 A1 | 7/2010 | Hancock et al. |
| 2010/0168741 A1 | 7/2010 | Sanai et al. |
| 2010/0179533 A1 | 7/2010 | Podhajsky |
| 2010/0179536 A1 | 7/2010 | Podhajsky et al. |
| 2010/0179538 A1 | 7/2010 | Podhajsky |
| 2010/0179541 A1 | 7/2010 | Joseph et al. |
| 2010/0179542 A1 | 7/2010 | Joseph et al. |
| 2010/0191233 A1 | 7/2010 | Wham et al. |
| 2010/0211063 A1 | 8/2010 | Wham et al. |
| 2010/0217258 A1 | 8/2010 | Floume et al. |
| 2010/0217264 A1 | 8/2010 | Odom et al. |
| 2010/0318079 A1 | 12/2010 | McPherson et al. |
| 2010/0318080 A1 | 12/2010 | Keppel |
| 2011/0028963 A1 | 2/2011 | Gilbert |
| 2011/0054460 A1 | 3/2011 | Gilbert |
| 2011/0060329 A1 | 3/2011 | Gilbert |
| 2011/0071516 A1 | 3/2011 | Gregg |
| 2011/0071521 A1 | 3/2011 | Gilbert |
| 2011/0077631 A1 | 3/2011 | Keller |
| 2011/0112530 A1 | 5/2011 | Keller |
| 2011/0115562 A1 | 5/2011 | Gilbert |
| 2011/0144635 A1 | 6/2011 | Harper et al. |
| 2011/0178516 A1 | 7/2011 | Orszulak et al. |
| 2011/0202056 A1 | 8/2011 | Sartor |
| 2011/0204903 A1 | 8/2011 | Gilbert |
| 2011/0208179 A1 | 8/2011 | Prakash et al. |
| 2011/0213354 A1 | 9/2011 | Smith |
| 2011/0213355 A1 | 9/2011 | Behnke, II |
| 2011/0301607 A1 | 12/2011 | Couture |
| 2011/0318948 A1 | 12/2011 | Plaven et al. |
| 2011/0319881 A1 | 12/2011 | Johnston |
| 2012/0004703 A1 | 1/2012 | Deborski et al. |
| 2012/0010610 A1 | 1/2012 | Keppel |
| 2012/0022521 A1 | 1/2012 | Odom et al. |
| 2012/0029515 A1 | 2/2012 | Couture |
| 2012/0089139 A1 | 4/2012 | Wham et al. |
| 2012/0101491 A1 | 4/2012 | Blaha |
| 2012/0116268 A1 | 5/2012 | Orszulak et al. |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4206433 | 9/1993 |
| DE | 4339049 | 5/1995 |
| DE | 19506363 | 8/1996 |
| DE | 19717411 | 11/1998 |
| DE | 19848540 | 5/2000 |
| DE | 10 2008 05873 | 4/2010 |
| EP | 246350 | 11/1987 |
| EP | 267403 | 5/1988 |
| EP | 296777 | 12/1988 |
| EP | 310431 | 4/1989 |
| EP | 325456 | 7/1989 |
| EP | 336742 | 10/1989 |
| EP | 390937 | 10/1990 |
| EP | 556705 | 8/1993 |
| EP | 569130 | 11/1993 |
| EP | 608609 | 8/1994 |
| EP | 640317 | 3/1995 |
| EP | 694291 | 1/1996 |
| EP | 617925 | 7/1996 |
| EP | 836868 | 4/1998 |
| EP | 878169 | 11/1998 |
| EP | 882955 | 12/1998 |
| EP | 1051948 | 11/2000 |
| EP | 1053720 | 11/2000 |
| EP | 1151725 | 11/2001 |
| EP | 1278007 | 1/2003 |
| EP | 1293171 | 3/2003 |
| EP | 1472984 | 11/2004 |
| EP | 1495712 | 1/2005 |
| EP | 1500378 | 1/2005 |
| EP | 1146827 | 3/2005 |
| EP | 1535581 | 6/2005 |
| EP | 870473 | 9/2005 |
| EP | 1609430 | 12/2005 |
| EP | 1366724 | 1/2006 |
| EP | 1707144 | 3/2006 |
| EP | 1645235 | 4/2006 |
| EP | 880220 | 6/2006 |
| EP | 1681026 | 7/2006 |
| EP | 1707143 | 10/2006 |
| EP | 1744354 | 1/2007 |
| EP | 1776929 | 4/2007 |
| EP | 1810628 | 7/2007 |
| EP | 1810630 | 7/2007 |
| EP | 1810631 | 7/2007 |
| EP | 1810632 | 7/2007 |
| EP | 1810633 | 7/2007 |
| EP | 1810634 | 7/2007 |
| EP | 1849425 | 10/2007 |
| EP | 1854423 | 11/2007 |
| EP | 1862137 | 12/2007 |
| EP | 2025297 | 5/2008 |
| EP | 1263181 | 9/2008 |
| EP | 1994904 | 11/2008 |
| EP | 2100566 | 9/2009 |
| EP | 2111812 | 10/2009 |
| EP | 2253286 | 11/2010 |
| EP | 1594392 | 6/2011 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| GB | 607850 | 9/1948 |
| GB | 702510 | 1/1954 |
| GB | 855459 | 11/1960 |
| GB | 902775 | 8/1962 |
| GB | 1290304 | 9/1972 |
| GB | 2154881 | 9/1985 |
| GB | 2164473 | 3/1986 |
| GB | 2214430 | 9/1989 |
| GB | 2331247 | 5/1999 |
| GB | 2358934 | 8/2001 |
| GB | 2434872 | 8/2007 |
| JP | 63 005876 | 1/1988 |
| SU | 166452 | 1/1965 |
| SU | 727201 | 4/1980 |
| WO | WO92/06642 | 4/1992 |
| WO | WO92/07622 | 5/1992 |
| WO | WO93/24066 | 12/1993 |
| WO | WO94/10922 | 5/1994 |
| WO | WO94/24949 | 11/1994 |
| WO | WO94/28809 | 12/1994 |
| WO | WO95/09577 | 4/1995 |
| WO | WO95/18575 | 7/1995 |
| WO | WO95/19148 | 7/1995 |
| WO | WO95/25471 | 9/1995 |
| WO | WO95/25472 | 9/1995 |
| WO | WO96/02180 | 2/1996 |

| WO | WO96/04860 | 2/1996 |
| WO | WO96/08794 | 3/1996 |
| WO | WO96/18349 | 6/1996 |
| WO | WO96/29946 | 10/1996 |
| WO | WO96/39085 | 12/1996 |
| WO | WO96/39086 | 12/1996 |
| WO | WO96/39088 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/10763 | 3/1997 |
| WO | WO97/11648 | 4/1997 |
| WO | WO97/17029 | 5/1997 |
| WO | WO97/43971 | 11/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO99/56647 | 11/1999 |
| WO | WO00/48672 | 8/2000 |
| WO | WO00/54683 | 9/2000 |
| WO | WO01/01847 | 1/2001 |
| WO | WO02/00129 | 1/2002 |
| WO | WO02/11634 | 2/2002 |
| WO | WO02/32333 | 4/2002 |
| WO | WO02/32335 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/047446 | 6/2003 |
| WO | WO03/090630 | 11/2003 |
| WO | WO03/090635 | 11/2003 |
| WO | WO03/092520 | 11/2003 |
| WO | WO2004/028385 | 4/2004 |
| WO | WO2004/098385 | 4/2004 |
| WO | WO2004/043240 | 5/2004 |
| WO | WO2004/047659 | 6/2004 |
| WO | WO2004/052182 | 6/2004 |
| WO | WO2004/073488 | 9/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060365 | 7/2005 |
| WO | WO2005/060849 | 7/2005 |
| WO | WO2005/115235 | 12/2005 |
| WO | WO2005/117735 | 12/2005 |
| WO | WO2006/050888 | 5/2006 |
| WO | WO2006/105121 | 10/2006 |
| WO | WO2007/055491 | 5/2007 |
| WO | WO2007/067522 | 6/2007 |
| WO | WO2007/105963 | 9/2007 |
| WO | WO2008/002517 | 1/2008 |
| WO | WO2008/003058 | 1/2008 |
| WO | WO2008/011575 | 1/2008 |
| WO | WO2008/043999 | 4/2008 |
| WO | WO2008/044000 | 4/2008 |
| WO | WO2008/044013 | 4/2008 |
| WO | WO2008/053532 | 5/2008 |
| WO | WO2008/070562 | 6/2008 |
| WO | WO2008/071914 | 6/2008 |
| WO | WO2008/101356 | 8/2008 |
| WO | WO2008/110756 | 9/2008 |

OTHER PUBLICATIONS

U.S. Appl. No. 10/406,690, filed Apr. 3, 2003, Robert J. Behnke, II.
U.S. Appl. No. 10/573,713, filed Mar. 28, 2006, Robert H. Wham.
U.S. Appl. No. 10/761,524, filed Jan. 21, 2004, Robert Wham.
U.S. Appl. No. 11/242,458, filed Oct. 3, 2005, Daniel J. Becker.
U.S. Appl. No. 12/985,063, filed Jan. 5, 2011, Robert J. Behnke, II.
U.S. Appl. No. 13/034,822, filed Feb. 25, 2011, Mark A. Johnston.
U.S. Appl. No. 13/048,639, filed Mar. 15, 2011, James S. Cunningham.
U.S. Appl. No. 13/049,459, filed Mar. 16, 2011, James H. Orszulak.
U.S. Appl. No. 13/050,770, filed Mar. 17, 2011, Robert B. Smith.
U.S. Appl. No. 13/085,258, filed Apr. 12, 2011, Ronald J. Podhajsky.
U.S. Appl. No. 13/085,278, filed Apr. 12, 2011, James A. Gilbert.
U.S. Appl. No. 13/118,973, filed May 31, 2011, James H. Orszulak.
U.S. Appl. No. 13/186,092, filed Jul. 19, 2011, George J. Collins.
U.S. Appl. No. 13/186,107, filed Jul. 19, 2011, George J. Collins.
U.S. Appl. No. 13/186,121, filed Jul. 19, 2011, George J. Collins.
U.S. Appl. No. 13/195,607, filed Aug. 1, 2011, James H. Orszulak.
U.S. Appl. No. 13/221,424, filed Aug. 30, 2011, James E. Krapohl.
U.S. Appl. No. 13/228,996, filed Sep. 9, 2011, Robert B. Smith.
U.S. Appl. No. 13/236,997, filed Sep. 20, 2011, Robert J. Behnke, II.
U.S. Appl. No. 13/237,068, filed Sep. 20, 2011, Robert J. Behnke, II.
U.S. Appl. No. 13/237,187, filed Sep. 20, 2011, Robert J. Behnke, II.
U.S. Appl. No. 13/237,342, filed Sep. 20, 2011, Robert J. Behnke, II.
U.S. Appl. No. 13/237,488, filed Sep. 20, 2011, Robert J. Behnke, II.
U.S. Appl. No. 13/247,043, filed Sep. 28, 2011, Donald W. Heckel.
U.S. Appl. No. 13/358,129, filed Jan. 25, 2012, Joseph D. Brannan.
U.S. Appl. No. 13/360,140, filed Jan. 27, 2012, James E. Krapohl.
U.S. Appl. No. 13/362,548, filed Jan. 31, 2012, Steven P. Buysse.
U.S. Appl. No. 13/362,816, filed Jan. 31, 2012, Steven P. Buysse.
U.S. Appl. No. 13/424,127, filed Mar. 19, 2012, Robert J. Behnke, II.
U.S. Appl. No. 13/426,204, filed Mar. 21, 2012, Robert B. Smith.
U.S. Appl. No. 13/442,460, filed Apr. 9, 2012, James E. Krapohl.
U.S. Appl. No. 13/446,096, filed Apr. 13, 2012, James H. Orszulak.
U.S. Appl. No. 13/469,960, filed May 11, 2012, Robert J. Behnke, II.
Wald et al, "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.

Cosman et al., "Radiofrequency Lesion Generation and Its Effect on Tissue Impedance" Applied Neurophysiology 51: (1988) pp. 230-242.

Zlatanovic M., "Sensors in Diffusion Plasma Processing" Microelectronics 1995; Proceedings. 1995; $20^{th}$ International Conference CE on Nis, Serbia Sep. 12-14, 1995; New York, NY vol. 2 pp. 565-570.

Ni W. et al. "A Signal Processing Method for the Coriolis Mass Flowmeter Based on a Normalized . . ." Journal of Applied Sciences-Yingyong Kexue Xuebao, Shangha CN, vol. 23 No. 2;(Mar. 2005); pp. 160-164.

Chicharo et al. "A Sliding Goertzel Algorith" Aug. 1996, pp. 283-297 Signal Processing, Elsevier Science Publishers B.V. Amsterdam, NL vol. 52 No. 3.

Bergdahl et al., "Studies on Coagulation and the Development of an Automatic Computerized Bipolar Coagulator" Journal of Neurosurgery 75:1, (Jul. 1991) pp. 148-151.

Cosman et al., "Theoretical Aspects of Radiofrequency Lesions in the Dorsal Root Entry Zone" Neurosurgery 15:(1984) pp. 945-950.

Goldberg et al., "Tissue Ablation with Radiofrequency: Effect of Probe Size, Gauge, Duration, and Temperature on Lesion Volume" Acad Radio (1995) vol. 2, No. 5, pp. 399-404.

Medtrex Brochure—Total Control at Full Speed, "The O.R. Pro 300" 1 p. Sep. 1998.

Valleylab Brochure "Valleylab Electroshield Monitoring System" 2 pp. Nov. 1995.

International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001494.9 dated Aug. 25, 2010.
International Search Report EP 07001494.9 extended dated Mar. 7, 2011.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09004250.8 dated Aug. 2, 2010.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400.9 dated Apr. 13, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP09763515.5 dated Nov. 29, 2011.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report EP10164740.2 dated Aug. 3, 2010.
International Search Report EP10171787.4 dated Nov. 18, 2010.
International Search Report EP10172636.2 dated Dec. 6, 2010.
International Search Report EP10174476.1 dated Nov. 12, 2010.
International Search Report EP10178287.8 dated Dec. 14, 2010.
International Search Report EP10179305.7 dated Aug. 23, 2011.
International Search Report EP10179321.4 dated Mar. 18, 2011.
International Search Report EP10179353.7 dated Dec. 21, 2010.
International Search Report EP10179363.6 dated Jan. 12, 2011.
International Search Report EP10180004.3 dated Jan. 5, 2011.
International Search Report EP10180964.8 dated Dec. 22, 2010.
International Search Report EP10180965.5 dated Jan. 26, 2011.
International Search Report EP10181018.2 dated Jan. 26, 2011.
International Search Report EP10181060.4 dated Jan. 26, 2011.
International Search Report EP10182003.3 dated Dec. 28, 2010.
International Search Report EP10182005.8 dated Jan. 5, 2011.
International Search Report EP10188190.2 dated Nov. 22, 2010.
International Search Report EP10191319.2 dated Feb. 22, 2011.
International Search Report EP10195393.3 dated Apr. 11, 2011.
International Search Report EP11006233.8 dated Feb. 2, 2012.
International Search Report EP11155959.7 dated Jun. 30, 2011.
International Search Report EP11155960.5 dated Jun. 10, 2011.
International Search Report EP11168660 dated Sep. 28, 2011.
International Search Report EP11170959.8 dated Dec. 9, 2011.
International Search Report EP11173562.7 dated Nov. 24, 2011.
International Search Report EP11182150.0 dated Nov. 17, 2011.
International Search Report EP11188798.0 dated Dec. 27, 2011.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.

SWITCHED RESONANT ULTRASONIC POWER AMPLIFIER SYSTEM

CROSS REFERENCE TO RELATED APPLICATIONS

This application is a continuation application of U.S. patent application Ser. No. 12/163,408 filed on Jun. 27, 2008 now U.S. Pat. No. 8,096,961, which is a continuation application of U.S. patent application Ser. No. 10/974,332 filed on Oct. 27, 2004, now U.S. Pat. No. 7,396,336 which claims the benefit of and priority to U.S. Provisional Patent Application Ser. No. 60/538,202 filed on Jan. 22, 2004, U.S. Provisional Patent Application Ser. No. 60/527,812 filed on Dec. 8, 2003, and U.S. Provisional Patent Application Ser. No. 60/515,826 filed on Oct. 30, 2003, the entire contents of which is incorporated by reference herein.

BACKGROUND OF THE INVENTION

1. Technical Field

The present disclosure relates to devices for amplifying an input signal and providing an output signal to a surgical instrument. More particularly, the present disclosure relates to a switched resonant ultrasonic power amplifier system for surgical instruments.

2. Background of Related Art

Conventional power amplifier circuits for supplying drive signals to ultrasonic transducers are susceptible to drift and droop in power delivery and variations in frequency when the ultrasonic transducer is exposed to changing loading conditions. Additionally, conventional power amplifier circuits require a relatively large footprint, are not lightweight, have efficiency problems, are generally complex circuits, and require heat sinking to dissipate heat generated during operation. Due to their relatively large size and radiated heat, placement of conventional power amplifier circuits may be problematic in a medical treatment facility. Therefore, a need exists for a power amplifier circuit to supply a drive signal to an ultrasonic transducer and which overcomes the problems of conventional power amplifiers.

SUMMARY

A switched resonant ultrasonic power amplifier system that has improved operating efficiency is provided. The switched resonant ultrasonic power amplifier system of the present disclosure has reduced heat generating characteristics and a smaller footprint than conventional power amplifiers. Furthermore, the switched resonant ultrasonic power amplifier system includes compensation circuitry for changing tissue loads during system operation, structure for frequency, phase, and gain stabilization and structure for ultrasonic power loss compensation.

The present disclosure relates to a switched resonant ultrasonic power amplifier system including a switched resonant power amplifier. The power amplifier system further includes a wave shaping circuit, a frequency generating and compensating circuit, and a compensated drive circuit. The switched resonant power amplifier generates a transducer driver signal for driving an ultrasonic transducer. The wave shaping circuit includes a zero crossing detector and a comparator. A feedback signal from the ultrasonic transducer is generally sinusoidal and is applied to an input of the zero crossing detector where it is transformed into a square wave. The square wave output of the zero crossing detector is capacitively coupled to the input of the comparator to form a reset signal.

The frequency generating and compensating circuit includes a reference timer and a phase-locked loop. The reset signal is applied to an input of the reference timer to generate a compensated reference signal having a substantially identical frequency that is further applied to an input of the phase-locked loop. The phase-locked loop outputs a compensated clock signal at a particular frequency that is controllable by the compensated reference signal applied to the input of the phase-locked loop. The compensated clock signal is generally at a different frequency than the desired output signal to be applied to the ultrasonic transducer.

The phase locked loop compares the compensated reference signal to a divider reference signal for generating a frequency error signal and/or a phase error signal. The phase locked loop provides frequency compensation by adjusting the compensated clock signal according to a value of the frequency error signal. In addition, it may include a phase delay circuit for adjusting the phase relationship between the compensated reference signal and the divider reference signal according to a value of the phase error signal. Generally, the phase locked loop receives digital input signals from the drive circuit and the wave shaping circuit. Alternatively, the phase locked loop may be configured and adapted for mixed-mode signal processing where the inputs are a combination of analog and digital signals. By advantageously adjusting the compensated clock signal for frequency and/or phase, the ultrasonic power amplifier system compensates the gain of the ultrasonic amplifier system.

The compensated clock signal is applied to an input of the compensated drive circuit. The compensated drive circuit includes a divider, a flip-flop, and a driver. A selected step-down ratio is applied to the compensated clock signal in the divider that results in a counter output signal delivered by the divider to the flip-flop, which has a lower frequency than the compensated clock signal. The counter output signal has a frequency that is approximately double the selected operating frequency for the ultrasonic transducer. A further reduction in frequency occurs as the counter output signal is applied to the flip-flop. The flip-flop generates two complementary square waves that are substantially 180° out-of-phase with respect to each other. Each of the square waves has a frequency that is at the selected operating frequency for the power amplifier and approximately one-half of the frequency of the counter output signal. These complementary square waves are applied to inputs of the driver for amplification and transmission to the inputs of the switched resonant power amplifier as driver output signals.

In another preferred embodiment, the driver includes a phase delay circuit that cooperates with the driver and provides phase compensation for the switched resonant power amplifier input signals. By controlling the phase relationship between the input signals, the driver is now phase correlated and random phase relationships are significantly minimized.

The switched resonant power amplifier includes a pair of insulated gate bi-polar transistors that receive the driver output signals. The insulated gate bi-polar transistors are biased such that when one is conducting the other one is not conducting, since one driver output signal has a value that corresponds to a "high" value, while the complementary driver output signal has a value that corresponds to a "low" value. When the driver signals change states (e.g., high to low and low to high), the respective insulated gate bi-polar transistors change from a conducting state to a non-conducting state, thereby providing an output to a primary side of an output transformer. On a secondary side of the output transformer is a pair of DC blocking output capacitors further coupled to an input of an ultrasonic device. The waveforms on the primary side of the output transformer are coupled across to a secondary side of the output transformer, where the waveforms combine to form the transducer driver signal. The ultrasonic device includes an ultrasonic transducer and a feedback transducer that are operatively coupled to the secondary side of the output transformer. The ultrasonic transducer receives the transducer drive signal from the output transformer and drives the transducer element to deliver the ultrasonic energy. The feedback transducer generates the feedback signal that is coupled to the wave shaping circuit.

In addition, the ultrasonic power amplifier system includes an output control circuit. The output control circuit includes the frequency generating and compensating circuit and the drive circuit. It cooperates with the wave shaping circuit for real time monitoring and control. The reset signal, that is representative of the feedback signal, is received by the frequency generating and compensating circuit for generating a compensated clock circuit. The divider reference signal is compared to the compensated reference signal in real time to control the compensated clock signal for frequency, phase, and/or gain. Additionally, the drive circuit includes a phase delay drive disposed in the driver for additional phase compensation between switched resonant power amplifier input signals. By providing real time monitoring and control of the drive signal to the ultrasonic device, the ultrasonic power amplifier system is capable of automatically monitoring and controlling the output of the ultrasonic device.

BRIEF DESCRIPTION OF THE DRAWINGS

Embodiments of the presently disclosed switched resonant ultrasonic power amplifier system are described herein with reference to the drawings, wherein.

DETAILED DESCRIPTION

Figure 1:
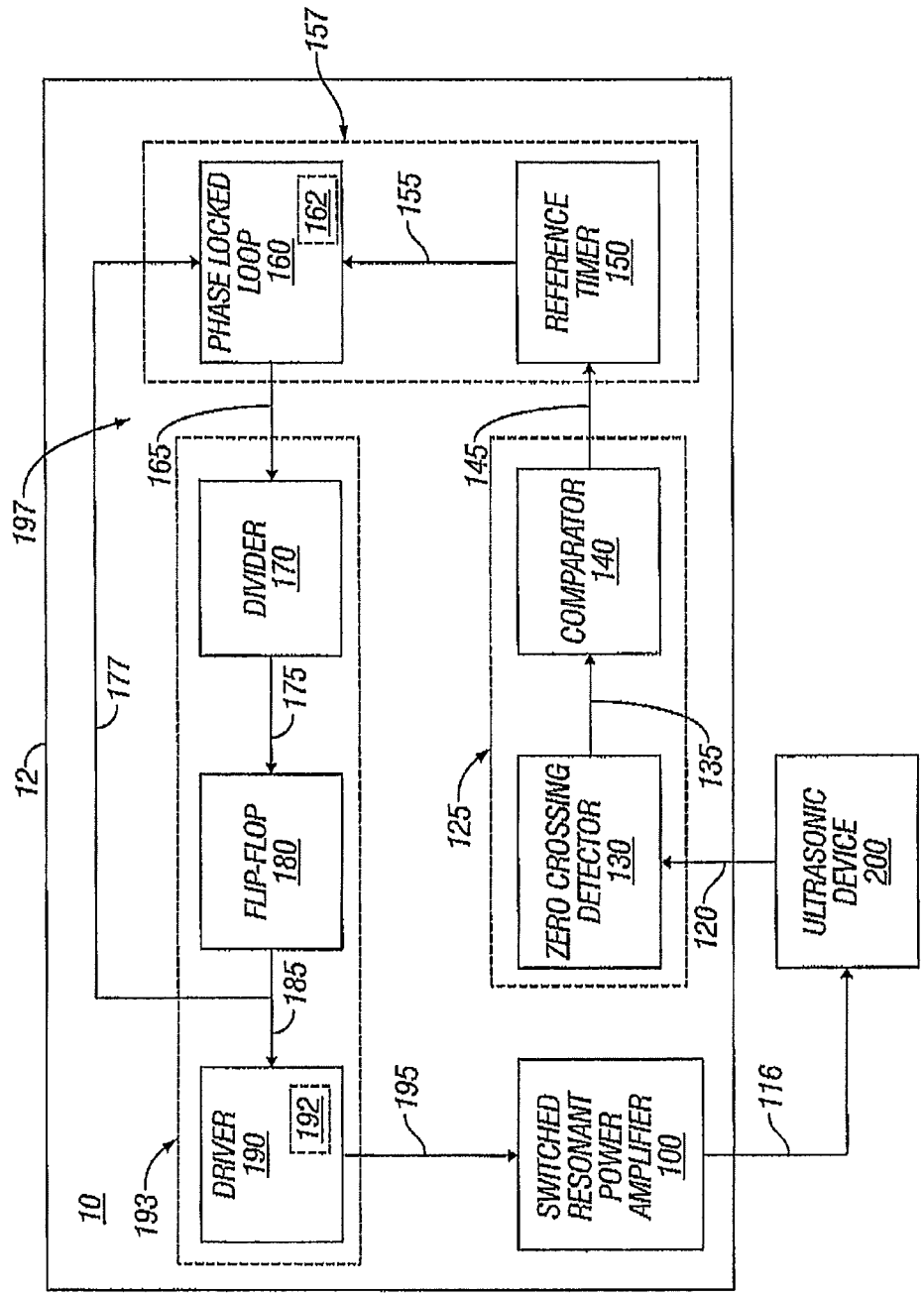
FIG. 1 is block diagram of a switched resonant ultrasonic power amplifier system in accordance with an embodiment of the present disclosure.

Embodiments of the presently disclosed switched resonant ultrasonic power amplifier system will now be described in detail with reference to the drawings, in which like reference numerals and characters designate identical or corresponding elements in each of the drawings.

As mentioned above, conventional power amplifier circuits, which supply drive signals to ultrasonic transducers, are typically susceptible to so-called "drift" and "droop" in power delivery and variations in frequency when the ultrasonic transducer is exposed to changing loading conditions. Moreover, conventional power amplifier circuits are typically very complex (e.g., complex circuitry), require a relatively large footprint and are quite burdensome, suffer from efficiency problems, and require a heat sink (or other cooling means) to dissipate heat generated during operation. As a result, placement of conventional power amplifier circuits may be problematic in a medical treatment facility.

Figure 2:
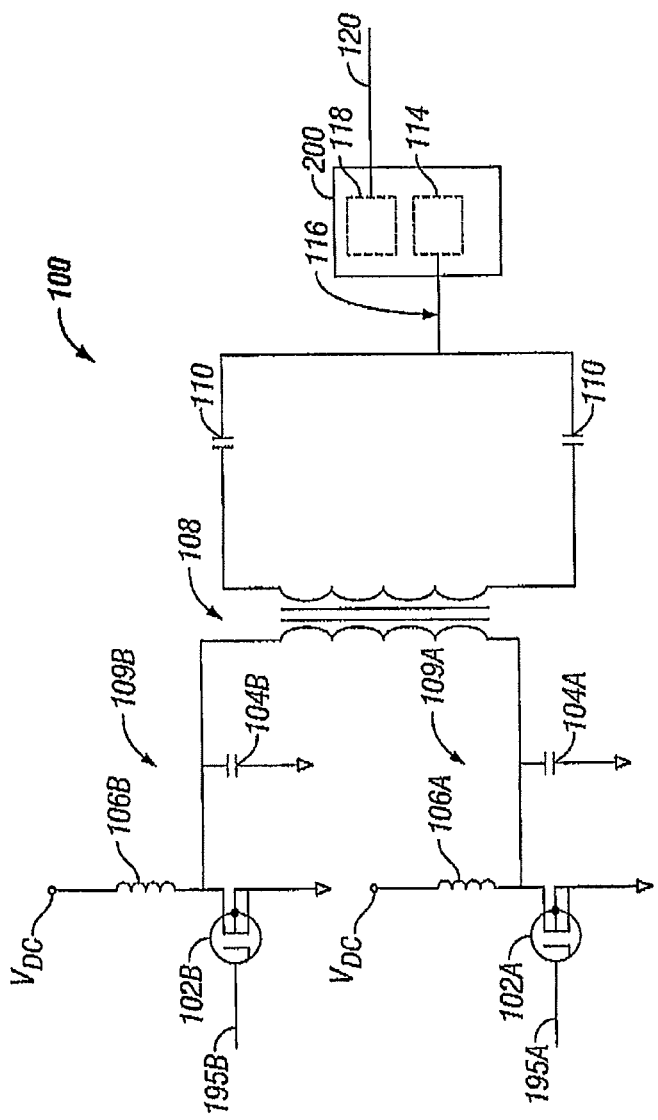
FIG. 2 is a schematic diagram of an embodiment of a switched resonant power amplifier of FIG. 1 in accordance with the present disclosure.

Referring to FIG. 1, an exemplary embodiment of the presently disclosed switched resonant ultrasonic power amplifier system 10 is illustrated. Switched resonant ultrasonic power amplifier system 10 is enclosed by box 12 in FIG. 1 and includes a switched resonant power amplifier 100, a wave shaping circuit 125 having a zero crossing detector 130 and a comparator 140, and a frequency generating and compensating circuit 157 having a reference timer 150 and a phase locked loop ("PLL") 160. The switched resonant ultrasonic power amplifier system 10 further includes a compensated drive circuit 193 having a divider 170, a flip-flop 180, and a driver 190. An ultrasonic device 200 includes an ultrasonic transducer 114 and a feedback transducer 118 (as shown in FIG. 2) for receiving a transducer driver signal 116 that is an output of the switched resonant power amplifier 100. Preferably, driver signal 116 is applied to ultrasonic transducer 114. A feedback signal 120 is generated by the feedback transducer 118 and is communicated to zero crossing detector 130. Feedback signal 120 is proportional to driver signal 116 with substantially similar phase and frequency values and generally lower voltage values.

As shown in FIG. 2, switched resonant power amplifier 100 includes a plurality of switching elements 102A, 102B; a corresponding number of resonant tuning components or elements including a tuning capacitor 104A, 104B and a tuning inductor 106A, 106B; and an output transformer 108. Tuning capacitors 104A, 104B and tuning inductors 106A, 106B form first and second tuning circuits 109A, 109B respectively. Output transformer 108 is operatively coupled to an input of ultrasonic transducer 114. A variety of devices may be used for switching elements 102A, 102B, including relays, metal oxide semiconductor field effect transistors ("MOSFET"), and insulated gate bipolar transistors ("IGBT").

In operation, driver 190 provides at least one driver output signal 195 that is coupled to the input of at least one switching element 102. Driver output signal 195 includes a corresponding number of input signals 195A, 195B to the number of switching elements 102A, 102B of switched resonant power amplifier 100. Each switching element 102A, 102B is capable of producing an amplified output of the respective input signals 195A, 195B. A supply voltage $V_{DC}$ is supplied through tuning inductors 106A, 106B to switching elements 102A, 102B where tuning inductors 106A, 106B are connected in a series relationship to a supply lead of each switching element 102A, 102B. Tuning capacitors 104A, 104B are connected in a parallel relationship to an output lead of each switching element 102A, 102B.

The amplified output of each switching element 102A, 102B is coupled to the corresponding tuning circuit 109A, 109B. Tuning capacitors 104A, 104B and tuning inductors 106A, 106B are selected to correspond to a particular resonant frequency of input signals 195A, 195B. For example, if the selected transducer driver signal 116 has a frequency of 23 KHz, i.e., a period of 43.5 μs, then the tuned period for each switching element 102A, 102B is 21.75 μs. The tuned period for tuning circuits 109A, 109B is defined by the formula $T=\pi(LC)^{1/2}$, where L is the value of tuning inductors 106A, 106B, C is the value of tuning capacitors 104A, 104B, and T is the tuned period.

Output transformer 108, in cooperation with output capacitors 110 couples the amplified output of switching elements 102A, 102B, or driver signal 116, to ultrasonic transducer 114. Output capacitors 110 are connected in a series arrangement with the secondary coil of output transformer 108. Using output capacitors 110 in a series arrangement substantially blocks any residual direct current ("DC") and passes substantially all the alternating current ("AC") on the secondary side of output transformer 108. Preferably, output transformer 108 has a ratio of approximately 1:1 while output capacitors 110 have a value of approximately 10 μf.

In a preferred embodiment, a pair of IGBTs, used as switching elements 102A, 102B, is disposed in switched resonant power amplifier 100. Driver 190 provides the pair of input signals 195A, 195B that are coupled to the gates of switching elements 102A, 102B. Input signals 195A, 195B are square waves that are approximately 180° out of phase with respect to each other. Supply voltage $V_{DC}$ is applied to the drains, or collectors, of switching elements 102A, 102B through series connected tuning inductors 106A, 106B. Tuning capacitors 104A, 104B are additionally connected in parallel to the drains, or collectors, thereby defining first and second tuning circuits 109A, 109B. Switching elements 102A, 102B further include sources, or emitters, that are connected to a chassis common. As each input signal 195A, 195B changes in value, a corresponding inverse change in the output of switching elements 102A, 102B occurs.

Each switching element 102A, 102B only conducts when each corresponding input signal 195A, 195B rises above a threshold value. Using a pair of switching elements 102A, 102B permits a first switching element 102A to conduct (e.g., a first input signal 195A is above the threshold value) while a second switching element 102B does not conduct (e.g., a second input signal 195B is at or below the threshold value), since the corresponding first and second input signals 195A, 195B are approximately 180° out of phase with respect to each other. After a period of time, corresponding to the period of first input signal 195A, has elapsed, first input signal 195A is now at or below the threshold value while second input signal 195B is above the threshold value. At this point, first switching element 102A stops conducting while second switching element 102B begins conducting, thereby providing a switching capability of switched resonant power amplifier 100.

Further still, each tuning circuit 109A, 109B is operatively coupled to the primary side of output transformer 108 and connected in a series relationship to the other tuning circuit 109B, 109A respectively. Selecting the values of L and C, for tuning inductors 106A, 106B and tuning capacitors 104A, 104B, respectively, determines the resonant frequency of first and second tuning circuits 109A, 109B, respectively.

In an exemplary embodiment, the resonant frequency of each tuning circuit 109A, 109B is tuned near to the operating frequency of each input signal 195A, 195B. When first switching element 102A is conducting, it generates a first output that is operatively coupled through first tuning circuit 109A. The output of first switching element 102A and its associated first tuning circuit 109A is operatively coupled to the primary side of output transformer 108 and is preferably an AC half sine wave.

Operation of second switching element 102B and tuning circuit 109B is substantially similar to the operation of first switching element 102A and first tuning circuit 109A as described above. Second switching element 102B does not conduct when first switching element 102A conducts, since input signal 195B is approximately 180° out of phase with respect to input signal 195A. Therefore, the output of switching element 102B is essentially an AC half sine waveform that is complementary to the output of switching element 102A and provides a substantially smooth combined sinusoidal output wave at the secondary side of output transformer 108. The output wave has a frequency that is substantially equal to the input frequency of input signals 195A, 195B.

Output transformer 108 is preferably configured for a 1:1 primary to secondary ratio where the output waveform is substantially equivalent in magnitude to the input waveform. Output capacitors 110 are connected to the secondary side of output transformer 108 and generally block any DC component of the output waveform that may be present on the secondary side of output transformer 108. In addition, output capacitors 110 conduct substantially the entire AC component of the output waveform, thereby contributing to the smooth sinusoidal AC output waveform. The downstream side of output capacitors 110 is connected to the ultrasonic transducer 114, which could be magnetostrictive, piezoelectric, or transducer structures as is known in the art.

Ultrasonic device 200 includes feedback transducer 118 for providing feedback signal 120 to wave shaping circuit 125. Output transformer 108 is electrically coupled to ultrasonic device 200 such that electrical power is delivered to ultrasonic transducer 114 as transducer driver signal 116 and converted to ultrasonic power. Furthermore, switched resonant power amplifier 100 generates transducer driver signal 116 with the desired signal characteristics (e.g., wave shape, amplitude, and/or frequency) and communicates it to an input of ultrasonic device 200. In a preferred embodiment, transducer driver signal 116 is a substantially smooth sinusoidal AC waveform with the desired signal characteristics for driving ultrasonic transducer 114.

Feedback transducer 118 is also disposed on the secondary side of output transformer 108 and generates feedback signal 120 that is electrically coupled to zero crossing detector 130. In a preferred embodiment, feedback signal 120 is a sample of transducer driver signal 116 having a waveform with substantially the same frequency and wave shape. Since feedback signal 120 and transducer driver signal 116 are coupled within the ultrasonic device 200, characteristics of feedback signal 120 are related to characteristics of transducer driver signal 116 and reflect changes in the characteristics of the transducer(s) (e.g., ultrasonic transducer 114 and/or feedback transducer 118) of the ultrasonic device 200. For example, if the frequency of transducer driver signal 116 increases with a corresponding decrease in its period, feedback signal 120 has a corresponding increase it its frequency and substantially matches the frequency change of transducer driver signal 116. Changes in other characteristics of transducer driver signal 116 result in corresponding changes to the respective characteristics of feedback signal 120.

Zero crossing detector 130, in cooperation with associated circuitry, modifies feedback signal 120 and provides an output that is substantially a square wave 135. In a preferred embodiment, zero crossing detector 130 includes a comparison circuit, such as an LM393 integrated circuit, having biasing circuitry and a diode coupled to the output of the comparison circuit. Preferably, feedback signal 120 is coupled to the input of the comparison circuit for providing a more stable output square wave 135. As a component of wave shaping circuit 125, zero crossing detector 130 receives an analog input signal (e.g., feedback signal 120) and produces a digital output signal (e.g., square wave 135).

By applying feedback signal 120 to an appropriate input lead of the comparison circuit, zero crossing detector 130 generates square wave 135 having a waveform representative of feedback signal 120. As feedback signal 120 transitions above a predetermined (zero) voltage reference point, thereby becoming more positive, the comparison circuit conducts and provides a positive portion of square wave 135. The output will be of substantially constant amplitude as long as feedback signal 120 is more positive than the zero reference point. When feedback signal 120 is at the zero reference point, there is no difference in voltage on the input leads of the comparison circuit, thereby causing the comparison circuit to stop conducting, and provide a zero output. As a result, the output of the comparison circuit rapidly changes from a constant positive value to zero, thereby providing a substantially instantaneous transition of the output signal.

Once feedback signal 120 transitions below the zero reference point, thereby becoming more negative, the comparison circuit again conducts and provides a negative portion of square wave 135. Zero crossing detector 130 is biased and configured to provide a rapid change from the constant positive amplitude to the constant negative amplitude forming the leading and trailing edges of square wave 135, such that the edges are substantially vertical. Feedback signal 120 and square wave 135 have substantially identical frequencies, even if their respective amplitudes are different.

Square wave 135 is coupled to comparator 140, where square wave 135 is preferably capacitively coupled to comparator 140. Comparator 140 includes a comparison circuit and is preferably coupled to a capacitor coupling circuit that generally blocks any DC component of square wave 135 from being transmitted from zero crossing detector 130 and transmits substantially the entire AC component of square wave 135 to comparator 140. In a preferred embodiment, comparator 140 includes an IC comparator, such as an LM393 along with associated biasing and feedback circuitry.

As the amplitude of square wave 135 goes positive past the zero voltage reference point, it biases comparator 140 such that the output of comparison circuit goes negative, thereby causing the output of comparator 140, a reset signal 145, to become more negative. A portion of reset signal 145 is coupled through the feedback circuitry to another input of the comparison circuit, thereby providing feedback to the comparison circuit to produce a more stable output (e.g., reset signal 145). Preferably, reset signal 145 has a substantially identical frequency to square wave 135 with a waveform that is substantially 180° out-of-phase with respect to square wave 135.

Reset signal 145 is communicated to an input of reference timer 150 for controlling a timing function of reference timer 150. As reset signal 145 drops below a predetermined reset threshold value, it causes reference timer 150 to reset. When reference timer 150 resets, it generates a compensated reference signal 155 having a substantially identical frequency to reset signal 145, square wave 135, and feedback signal 120. Compensated reference signal 155 does not have the same phase characteristics as reset signal 145, but is essentially 180° out-of-phase with respect to reset signal 145 and feedback signal 120. Consequently, compensated reference signal 155 is substantially in phase with square wave 135.

In an exemplary embodiment, reference timer 150 includes an IC timer, such as a 555 precision timer, having associated biasing and feedback circuitry. Reference timer 150 in cooperation with the biasing circuitry is configured for operation as an astable multivibrator that produces a square wave output. Frequency and amplitude characteristics of the square wave are determined by the biasing circuit and the signal applied to a reset input of reference timer 150. According to an exemplary embodiment of the present disclosure, reset signal 145 is applied to a reset input of reference timer 150 to produce compensated reference signal 155. Combining the biasing configuration for the reference timer 150 in cooperation with reset signal 145 yields compensated reference signal 155 that has substantially the same frequency as feedback signal 120.

In a preferred embodiment, the 555 precision timer and the associated biasing circuitry of reference timer 150 are configured to generate compensated reference signal 155 that has a frequency lower than the selected operating frequency of switched resonant ultrasonic power amplifier system 10. More specifically, the 555 precision timer and its associated biasing circuitry are configured so that when the frequency of reset signal 145 is below the frequency of compensated reference signal 155, the biasing circuitry determines (e.g., controls) the frequency value of compensated reference signal 155 for providing compensation. In the situation where reset signal 145 has a higher frequency value than compensated reference signal 155, reset signal 145 acts as a trigger for the 555 precision timer causing a corresponding increase in the frequency of compensated reference signal 155.

An input of PLL 160 is coupled to an output of reference timer 150 for communicating compensated reference signal 155. PLL 160 receives compensated reference signal 155 and compares it to a divider reference signal 177. When reference signal 155 and divider reference signal 177 have substantially identical frequencies, PLL 160 produces a compensated clock signal 165 having a set frequency that corresponds to the frequency of the reference signal 155 and divider reference signal 177. In the situation where compensated reference signal 155 has a higher frequency than divider reference signal 177, PLL 160 lowers the frequency of compensated clock signal 165 as described below. Conversely, when compensated reference signal 155 has a lower frequency than divider reference signal 177, PLL 160 raises the frequency of compensated clock signal 165 as described below.

Advantageously, PLL 160 includes an IC PLL, such as a 4046 PLL IC chip, and associated biasing circuitry. In a preferred embodiment using PLL 160, compensated reference signal 155 is coupled to a signal input of the PLL 160 while divider reference signal 177 is applied to a reference input of PLL 160. Compensated clock signal 165 is generated by a voltage-controlled oscillator internal to PLL 160 chip and tuned to an output frequency. Internally, the frequencies of compensated reference signal 155 and divider reference signal 177 are compared to produce a frequency error signal at a phase comparator output of PLL 160.

This frequency error signal is applied to the voltage controlled oscillator input for adjusting the output frequency of the voltage controlled oscillator. If compensated reference signal 155 has a greater frequency than divider reference signal 177, the frequency error signal applied to the voltage controlled oscillator causes a decrease in the output frequency of compensated clock signal 165. In the situation where compensated reference signal 155 has a lower frequency than divider reference signal 177, the frequency error signal applied to the voltage controlled oscillator results in an increase of the output frequency of compensated clock signal 165.

While the above embodiment provides frequency compensation for compensated clock signal 165, it may also be desirable to provide phase compensation for clock signal 165. Frequency generating and compensating circuit 157 receives reset signal 145, which is representative of the output of ultrasonic device 200. As in the previous embodiment, reset signal 145 controls the generation of compensated reference signal 155 that has substantially the same phase and frequency as feedback signal 120. PLL 160 receives compensated reference signal 155 and compares it to divider reference signal 177, which is representative of compensated clock signal 165, thereby producing a phase error signal. When the phase difference between compensated reference signal 155 and divider reference signal 177 is at a minimum value (e.g., substantially in-phase), the phase error signal will have a low or first value. In situations where the phase difference between the signals is at a maximum value (e.g., substantially out-of-phase), the phase error signal will have a high or second value. If the phase difference between compensated reference signal 155 and divider reference signal 177 is between the maximum and minimum values, the phase error signal will have a value between the first and second values that is representative of the phase difference between the signals.

The phase error signal cooperates with associated circuitry in PLL 160 to adjust the timing of compensated clock signal 165 and thereby its phase relationship to compensated reference signal 155. More particularly, a delay circuit 162, such as that discussed in detail below, is included in PLL 160 to control the timing of compensated clock signal 165 for adjusting the phase timing of compensated clock signal 165 in accordance with the phase error signal. When the phase error signal indicates that compensated reference signal 155 does not have the desired phase relationship to divider reference signal 177, the delay circuit 162 of PLL 160 adjusts the phase timing of compensated clock signal 165 to change the phase relationship between them and preferably synchronize them. Changes to the timing of compensated clock signal 165 are reflected in divider reference signal 177 that is operatively coupled to PLL 160. In preferred embodiments, compensated reference signal 155 and compensated clock signal 165 are substantially in-phase with one another, thereby generating a phase error signal having a minimum value.

The PLL 160 may be configured and adapted to process signals that are analog, digital or a combination thereof. In this configuration, inputs to PLL 160 may be analog signals, digital signals, or a combination of analog and digital signals (e.g., mixed-mode). In the previous embodiment, the inputs were digital signals (e.g., compensated reference signal 155 and divider reference signal 177) that were processed by PLL 160. In the mixed-mode configuration, PLL 160 receives an analog input signal (e.g., feedback signal 120 directly from ultrasonic device 200) and compares it to an analog or digital reference signal, such as divider reference signal 177, as in the previous embodiment, for generating the frequency error signal and/or the phase error signal and adjusting the compensated clock signal accordingly.

In exemplary embodiments of the present disclosure, frequency generating and compensating circuit 157 includes frequency and phase compensation as discussed hereinabove. The frequency and phase compensation may be provided substantially simultaneously. By advantageously providing frequency and/or phase compensation, ultrasonic power amplifier system 10 provides gain compensation for reset signal 145 since the desired frequency and/or phase of compensated clock signal 165 is maintained during operation of ultrasonic power amplifier system 10. Furthermore, power compensation is provided, such as when adjustment and compensation of frequency, gain and/or phase (preferably frequency, gain and phase) is optimized. In addition, compensation for changing tissue loads is advantageously provided, since tissue loading changes the "tune", i.e., the natural frequency of the transducer system (e.g., ultrasonic transducer 114 and/or feedback transducer 118), which is being adjusted and compensated for by the switched resonant ultrasonic power amplifier system 10.

By way of example only, assume that the desired frequency is 23 KHz and compensated clock signal 165 has a frequency of 1 MHz that is sampled and output from flip-flop 180 as divider reference signal 177. When divider reference signal 177 and compensated reference signal 155 have substantially matching frequencies, the frequency error signal is essentially zero. Therefore, the voltage controlled oscillator continues to generate compensated clock signal 165 at a frequency of 1 MHz. If compensated reference signal 155 has a frequency greater than the 23 KHz of divider reference signal 177, then the frequency error signal causes the voltage-controlled oscillator to decrease the frequency of compensated clock signal 165 below 1 MHz. This decreases the frequency of divider reference signal 177 to match the frequency of compensated reference signal 155, thereby returning switched resonant ultrasonic power amplifier system 10 to a state of equilibrium at the desired frequency. By using PLL 160 to correct changes in frequency as in the above-given example, switched resonant ultrasonic power amplifier system 10 automatically adjusts in real time for frequency variations due to changing load conditions, power supply variations, or other frequency shifting conditions. In a similar manner, PLL 160 automatically adjusts and compensates for phase differences between compensated clock signal 165 and divider reference signal 177.

The output of PLL 160, e.g., compensated clock signal 165, is coupled to an input of compensated drive circuit 193, and preferably, to an input of divider 170 where the frequency of compensated clock signal 165 is stepped-down by divider 170 to a desired counter output signal 175. Divider 170 is configurable, using a plurality of input to output ratios, to step-down compensated clock signal 165 to one of a multitude of different output frequencies. Therefore, switched resonant ultrasonic power amplifier system 10 is adaptable for a number of different applications, devices or systems using different desired frequencies.

In an exemplary embodiment, divider 170 is a 4059 programmable divide-by-n counter chip having associated biasing circuitry. A clock input receives compensated clock signal 165 for processing by divider 170. Biasing circuitry for divider 170 establishes the step-down ratio for divider 170 and reduces the frequency of compensated clock signal 165 to a desired frequency for counter output signal 175.

Advantageously, the associated biasing circuitry is operatively coupled for programming the step-down ratio where the biasing circuitry is controllable by software and/or hardware switches. Hardware switches allow the operator to manually change the step-down ratio of divider 170 and adjust for different frequency outputs of switched resonant power amplifier system 10. Using software switches to control the biasing circuitry allows remote operation of the step-down ratio and further permits automatic control of the biasing circuitry by associated circuitry coupled to switched resonant power amplifier system 10, thereby improving the flexibility and adaptability of switched resonant power amplifier system 10.

Coupled to the output of divider 170 is flip-flop 180 for splitting counter output signal 175 into complementary square waves (e.g., each square wave is substantially 180° out-of-phase with respect to the other square wave) where each square wave has a frequency that is substantially one-half of the frequency of counter output signal 175. A portion or sample of one of the output square waves is diverted to a comparator input of PLL 160 as divider reference signal 177, which is discussed above. Preferably, flip-flop 180 is a quadruple D-type flip-flop with clear, such as a 74HC175 integrated circuit with associated biasing circuitry.

Flip-flop 180 is biased such that when counter output signal 175 is applied to a clock input of flip-flop 180, the flip-flop 180 outputs Q and ^Q, which are substantially 180° out-of-phase with respect to each other. Additionally, the output ^Q is coupled to a data input of flip-flop 180 for biasing flip-flop 180. By using ^Q as the input to the data input, the outputs Q and ^Q are toggled by counter output signal 175 such that each of the outputs Q and ^Q are substantially 180° out-of-phase with respect to each other and substantially one-half of the input frequency of counter output signal 175. Preferably, the output Q is sampled as divider reference signal 177 for supplying a frequency comparison signal to PLL 160 as discussed above.

A driver input signal 185 is the output of flip-flop 180 and is further coupled to an input of driver 190. Driver 190 amplifies driver input signal 185 to supply driver output signal 195 to switched resonant power amplifier 100. Preferably, driver 190 is selected for amplifying driver input signal 185 to match the desired input characteristics for switched resonant power amplifier 100.

In a preferred embodiment, driver 190 includes a CMOS MOSFET driver such as the MIC4424 along with associated biasing circuitry. Driver 190 has electronic characteristics that are preferred for use with the switching elements 102A, 102B (e.g., IGBTs) of switched resonant power amplifier 100. Driver input signal 185 includes the outputs Q and ^Q that are coupled to inputs A and B, respectively, of the driver 190 as shown in FIG. 2. Driver 190, in cooperation with its biasing circuitry, amplifies the components (Q and ^Q) of driver input signal 185 and communicates the amplified signals to outputs A and B as driver signals. The amplified signals substantially maintain their frequency and phase characteristics during the amplification process. Outputs A and B are combined to form driver output signal 195 and are coupled to the inputs of switched resonant power amplifier 100 as input signals 195A, 195B.

Additional frequency stability is provided by combining wave shaping circuit 125 with frequency generating and compensating circuit 157 to provide a desired frequency and/or phase compensated input signal to driver 190. By advantageously matching driver 190 to switched resonant power amplifier 100, proper coupling between driver input signal 185 and switched resonant power amplifier input signals 195A, 195B is obtained thereby effecting the desired amplification by switched resonant power amplifier 100.

In another preferred embodiment, driver 190 includes one or more components and/or circuits to form a phase delay circuit 192 as are known in the art. One such circuit includes two 555 timers (not shown) connected in series and associated biasing components. Alternatively, the 555 timers may be replaced by a 556 timer, which includes two 555 timers. Another example of a delay circuit includes two 74121 integrated circuits and associated biasing components. Preferably, the biasing circuitry in phase delay circuit 192 includes components that are adjustable by the system and/or the operator for adjusting the phase relationship between switched resonant power amplifier input signals 195A, 195B and/or the pulse widths of the input signals 195A, 195B. Advantageously, the above-mentioned delay circuits are capable of producing an output signal that is time delayed with respect to the input signal. In addition, each of the above-mention circuits is capable of producing an output signal that has a width that is less than, greater than, or equal to the input signal's width.

Phase delay circuit 192 advantageously cooperates with driver 190 for controlling the phase relationship between switched resonant power amplifier input signals 195A, 195B and for controlling their respective pulse widths. In the previous embodiment, switched resonant power amplifier input signals 195A, 195B were substantially 180° out-of-phase with respect to each other. However, by adding phase delay circuit 192 to driver 190, the timing and the pulse widths of each of the switched resonant power amplifier input signals 195A, 195B is controllable. In preferred embodiments, the phase relationship between switched resonant power amplifier input signals 195A and 195B is variable between about 0° to a value about 360°, while the pulse widths of the input signals 195A and 195B are substantially equal to one another. By adjusting the phase relationship and the pulse widths, ultrasonic power amplifier system 10 regulates an output from ultrasonic device 200 having the desired characteristics for a particular procedure.

When the phase relationship between switched resonant power amplifier input signals 195A and 195B is modified, drive signal 116 is pulsed and the ultrasonic power amplifier system 10, in turn, produces a pulsed output from ultrasonic device 200 rather than a substantially continuous output, where the time delay between the output pulses is proportional to the phase relationship. The duration of pulses output by ultrasonic device 200 is adjustable by changing the pulse widths of input signals 195A, 195B. Numerous advantageous combinations of pulse width and phase relationship may be used in ultrasonic power amplifier system 10 depending on the particular procedure.

Additionally, driver 190 in cooperation with phase delay drive 192 provides phase correlation between switched resonant power amplifier input signals 195A, 195B. Since the desired phase relationship is established and maintained between the input signals 195A and 195B by phase delay circuit 192, random or undesirable phase relationships between the input signals is significantly minimized.

Changes in the loading characteristics of transducer driver signal 116 caused by changes in the loading of ultrasonic device 200 are fed back to zero crossing detector 130 as changes in feedback signal 120. By way of example only, if ultrasonic device 200 is rapidly unloaded, its operating frequency rises and is reflected as a frequency rise in feedback signal 120. This increase in the operating frequency of ultrasonic device 200 is communicated to feedback transducer 118 with a corresponding frequency increase in feedback signal 120. As discussed in detail hereinabove, as feedback signal 120 increases in frequency, zero crossing detector 130 generates square wave 135 having a corresponding increase in frequency. The increased frequency of square wave 135 is capacitively coupled to comparator 140 for generating reset signal 145 that reflects the frequency increase in feedback signal 120. In cooperation with reference timer 150, the increased frequency of reset signal 145 raises the frequency of compensated reference signal 155 that is communicated to PLL 160.

An increased frequency input to PLL 160, as evidenced by the increased frequency of compensated reference signal 155, causes PLL 160 to raise compensated clock signal 165. A higher frequency of compensated clock signal 165 is transferred to an input of divider 170 thereby causing a corresponding increase in the frequency of counter output signal 175 that is communicated to flip-flop 180. Output from flip-flop 180 is supplied as driver input signal 185 and as driver reference signal 177, both signals having increased frequency. The resulting increase in the frequency of driver input signal 185 is applied to driver 190 and raises the frequency of driver output signal 195. By raising the frequency of driver output signal 195, switched resonant power amplifier 100 produces a higher frequency transducer driver signal 116 in response. Preferably, the higher frequency of transducer driver signal 116 is substantially identical to the frequency of frequency feedback signal 120, thereby returning power amplifier 10 to a steady-state equilibrium condition where transducer driver signal 116 and feedback signal 120 are at the substantially identical frequency.

By actively monitoring the output of ultrasonic device 200 through feedback signal 120 and adjusting driver signal 116 in response thereto, ultrasonic power amplifier system 10 automatically adjusts the output of ultrasonic device 200 in response to changes in operating parameters in real time. More specifically, ultrasonic power amplifier system 10 includes an output control circuit 197 that includes frequency generating and compensating circuit 157 and drive circuit 193. Output control circuit 197 receives reset signal 145 and generates switched resonant power amplifier input signals 195A, 195B having the desired frequency, phase, and/or gain compensation as discussed in detail above.

By advantageously selecting and using solid-state and/or semi-conductor components, switched resonant power amplifier system 10 can be made to have a smaller footprint, or size, than a conventional power amplifier circuit for a comparable output. In addition, switched resonant power amplifier system 10 produces less heat and is more efficient than prior art systems due to the use of solid-state and/or semi-conductor components in the system.

Although the illustrative embodiments of the present disclosure have been described herein with reference to the accompanying drawings, it is to be understood that the disclosure is not limited to those precise embodiments, and that various other changes and modifications may be affected therein by one skilled in the art without departing from the scope or spirit of the disclosure. All such changes and modifications are intended to be included within the scope of the disclosure.

What is claimed is:

1. A system for controlling an output of an ultrasonic device, the system comprising:
    an amplifier configured to receive and process a driver output signal that drives an ultrasonic device and controls the output thereof;
    an output control circuit configured to receive and process a feedback signal generated by the ultrasonic device or a divider reference signal that generates a compensated clock signal adjusted for phase or frequency differences between the feedback signal and the divider reference signal;
    a compensated drive circuit including divider circuitry for stepping down the frequency of the compensated clock signal to a selectable frequency that generates a counter output signal and flip-flop circuitry for splitting the counter output signal into first and second complementary square waves together forming a driver input signal; and
    a driver that amplifies the driver input signal and generates the counter output signal, wherein the driver includes a phase delay circuit that selectively adjusts the phase relationship between the first and second complementary square waves of the counter output signal or the pulse width of pulses of at least one of the first and second complementary square waves of the counter output signal.

2. The system of claim 1, wherein a sample of at least one of the first and second complementary square waves is the divider reference signal.

3. The system of claim 1, wherein the feedback signal is indicative of the output of the ultrasonic device, and the output of the ultrasonic device is controlled in real time.

4. The system of claim 3, wherein the switched resonant power amplifier includes at least one tuning circuit having a tuning period selected to correspond to a particular resonant frequency of the driver output signal.

5. The system of claim 1, wherein the amplifier is a switched resonant power amplifier.

6. The system of claim 5, wherein the switched resonant power amplifier includes a transformer having primary and secondary windings, wherein the driver output signal is coupled to the secondary winding of the transformer.

7. The system of claim 1, wherein the output control circuit includes a wave shaping circuit that receives and processes the feedback signal and generates a square wave reset signal having a substantially identical frequency to the feedback signal.

8. The system of claim 7, wherein the square wave reset signal has a waveform that is substantially 180° out-of-phase with respect to the feedback signal.

9. The system of claim 7, wherein the wave shaping circuit comprises:
    a zero crossing detector that receives and processes the feedback signal and generates a corresponding square wave signal; and
    a comparator that compares the square wave signal to a reference signal for generating the reset signal.

10. The system of claim 1, wherein the output control circuit further includes a compensating circuit operatively coupled to the compensated drive circuit, the compensating circuit having a phase locked loop (PLL).

11. The system of claim 10, wherein the PLL processes at least one analog signal and outputs the compensated clock signal.

12. The system of claim 11, wherein the PLL generates at least one of a frequency error signal or a phase error signal to compensate the compensated clock signal for at least one of phase and frequency relative to the compensated reference signal.

13. The system of claim 12, wherein the PLL includes delay circuitry that adjusts the phase of the compensated clock signal in accordance with the phase error signal.

14. The system of claim 1, wherein the amplifier includes first and second switching elements that are configured to receive the driver output signal, and the first and second complementary square waves of the driver output signal are coupled to the first and second switching elements, respectively.

15. The system of claim 1, wherein adjustment of the phase delay circuit controls the output of the ultrasonic device and produces a pulsed output from the ultrasonic device.

* * * * *